United States Patent [19]

Rose et al.

[11] Patent Number: 4,800,036
[45] Date of Patent: Jan. 24, 1989

[54] AQUEOUS BLEACH COMPOSITIONS THICKENED WITH A VISCOELASTIC SURFACTANT

[75] Inventors: Gene D. Rose; Arthur S. Teot; Kenneth L. Foster, all of Midland, Mich.

[73] Assignee: The Dow Chemical Company, Midland, Mich.

[21] Appl. No.: 939,338

[22] Filed: Dec. 8, 1986

Related U.S. Application Data

[63] Continuation-in-part of Ser. No. 732,013, May 6, 1985, abandoned, which is a continuation-in-part of Ser. No. 715,304, Mar. 25, 1985, abandoned.

[51] Int. Cl.$^4$ .......................... A61L 2/18; C11D 1/86; C11D 3/395; C11D 3/48
[52] U.S. Cl. ...................................... 252/102; 252/90; 252/95; 252/106; 252/187.2; 252/187.23; 252/187.26; 252/187.28; 252/187.31; 252/545; 252/546; 252/547; 252/DIG. 10; 252/DIG. 14
[58] Field of Search ......... 252/90, 102, 106, DIG. 14, 252/8.75, 527, 547, 173, 95, 187.2, 187.23, 187.26, 187.28, 187.31, 545, 546

[56] References Cited

U.S. PATENT DOCUMENTS

| | | | |
|---|---|---|---|
| 2,732,398 | 1/1956 | Brice et al. | 252/71 |
| 3,201,311 | 8/1965 | Antonides | 252/102 |
| 3,265,624 | 8/1966 | Inamorato | 252/102 |
| 3,325,414 | 6/1967 | Inamorato | 252/539 |
| 3,684,722 | 8/1972 | Hynam et al. | 252/98 |
| 3,749,673 | 7/1973 | Jones | 252/8.74 |
| 4,005,027 | 1/1977 | Hartman | 252/95 |
| 4,013,228 | 3/1977 | Schneider | 239/401 |
| 4,045,358 | 8/1977 | Ramachandran | 252/8.6 |
| 4,166,794 | 9/1979 | Grey | 252/8.8 |
| 4,255,273 | 3/1981 | Sakkab | 252/102 |
| 4,271,030 | 6/1981 | Brierley | 252/98 |
| 4,282,109 | 8/1981 | Citrone | 252/102 |
| 4,347,153 | 8/1982 | Hooper | 252/174.25 |
| 4,388,204 | 6/1983 | Diamond et al. | 252/98 |
| 4,390,448 | 6/1983 | Boden et al. | 252/187.26 |
| 4,460,487 | 7/1984 | Robinson | 252/8.8 |
| 4,461,652 | 7/1984 | Richmond | 134/2 |
| 4,463,905 | 8/1974 | Stoesser | 239/329 |
| 4,534,875 | 8/1985 | Rose | 252/71 |
| 4,576,728 | 3/1986 | Stoddart | 252/102 |
| 4,615,825 | 10/1986 | Teot et al. | 252/356 |

FOREIGN PATENT DOCUMENTS

| | | |
|---|---|---|
| 110544 | 6/1984 | European Pat. Off. . |
| 55-007218 | 6/1978 | Japan ................ 252/102 |
| 1466560 | 3/1977 | United Kingdom . |

*Primary Examiner*—Dennis Albrecht

[57] ABSTRACT

Bleach compositions, such as aqueous sodium hypochlorite formulations, are thickened by admixing the composition with a viscoelastic surfactant. Visco-elastic surfactants comprise surfactant ions and organic counterions that associate in the bleach composition to form the viscoelastic surfactant. Thickened bleach compositions of this invention exhibit bleach stability, phase stability, and viscosity stability for acceptably long periods of time. The thickened bleach compositions can be employed as nonmisting sprays and streams which will stick to vertical surfaces without substantial dripping and can be applied to various substrates using a dispensing device.

22 Claims, No Drawings

AQUEOUS BLEACH COMPOSITIONS THICKENED WITH A VISCOELASTIC SURFACTANT

CROSS-REFERENCE TO RELATED APPLICATIONS

This is a continatuion-in-part of U.S. patent application Ser. No. 732,013, filed May 6, 1985, now abandoned which is in turn a continuation-in-part of U.S. patent application Ser. No. 715,304, filed Mar. 25, 1985, also abandoned.

BACKGROUND OF THE INVENTION

The present invention relates to bleach compositions. In particular, it relates to thickened bleach compositions and the method of thickening them.

Bleach compositions are typically aqueous solutions of alkali metal and alkali earth metal hypochlorites. They are useful as cleaning agents, disinfectants, bactericides and fungicides. For example, bleach compositions are useful for cleaning textiles; dishes and glassware; and sinks, bathtubs and numerous other porcelain items.

Bleach compositions contain mostly water and therefore have viscosities similar to water. Unfortunately, it is often necessary to apply bleach compositions to vertical or inclined surfaces. Because the composition has low viscosity, it will not adhere to a vertical or inclined surface. A thickened bleach composition would be desirable if it could be easily applied, for example by spraying, and could adhere to a vertical or inclined surface without dripping. Thickened bleach compositions are disclosed in U.S. Pat. Nos. 4,388,204; 4,390,448; EPO Application No. 110,544 and Britich Patent No. 1,466,560. The bleach compositions of the references use various detergents or surface-active agents to thicken the composition. However, no one or two component surfactant additive system has proven satisfactory with regard to phase stability, bleach stability, and viscosity stability. Therefore, it would be desirable to provide a thickened bleach composition that employs only a one or two component additive system and exhibits good phase stability and bleach stability, as well as viscosity stability.

Bleach compositions are often applied to numerous items using dispensers like the manually operated atomizing dispensers disclosed in U.S. Pat. No. 4,463,905. Unfortunately, when typical bleach compositions are employed as a spray using such a dispenser, they can form an undesirable mist. This mist can cause problems if the vapors are inhaled, since the vapors can be disaggreably strong, as well as injurious to health. In addition, the mist can drift undesirably onto unprotected surfaces. For example, it can come into contact with clothing and other fabrics, skin and eyes, etc. Therefore, it would be desirable to provide a thickened bleach composition that can be employed as a substantially nonmisting spray while still maintaining its stability.

SUMMARY OF THE INVENTION

Accordingly, in one aspect, the present invention is a method of thickening an aqueous bleach composition containing a bleaching agent, comprising the step of contacting the composition with surfactant ions and organic counterions to form an aqueous solution under suitable solution conditions whereby the surfactant ions and organic counterions associate in the bleach composition thereby forming a viscoelastic surfactant.

In another aspect, the present invention is a thickened aqueous bleach composition made according to the method described above comprising a bleaching agent surfactant ions and organic counterions, and water; the components of the composition being combined to form an aqueous solution under suitable solution conditions whereby the surfactant ions and organic counterions associate in the bleach composition thereby forming a viscoelectric surfactant.

The addition of excess organic counterions to the bleach composition in accordance with the practice of this invention can further increase its viscosity, increase its viscosity stability at higher temperatures, or both.

The thickened bleach compositions of this invention are useful because they exhibit good phase stability, bleach stability, and viscosity stability, and they will adhere to a vertical or inclined surface without dripping. They are also useful because they can be employed as a substantially non-misting spray.

DETAILED DESCRIPTION OF THE INVENTION

This invention allows the skilled artisan to produce a thickened bleach composition. It also allows the skilled artisan to apply the composition in the form of a spray to a surface by expelling the composition from a dispensing device. The thickened or gelled bleach composition can be expelled from the dispenser easily despite its thickened character because the composition is thickened with a viscoelastic surfactant that can provide a shear thinning behavior. However, the viscoelastic surfactant is also shear stable, thus allowing the bleach composition to thicken after it is expelled from the dispenser, as for example, when the composition is applied to a surface. Therefore, the bleach composition can be applied to a vertical surface without substantial running or dripping. In addition, the bleach composition can be applied in the form of a stream or spray to a surface without the formation of an undesirable mist as the composition is expelled from a dispenser.

As used herein, the term "bleach composition" refers to an aqueous liquid that contains a bleach active agent. Such agents include hydrogen peroxide, potassium perchlorate, sodium hypochlorite, sodium peroxide, sodium chlorite, calcium hypochlorite (i.e., chlorinated lime), sodium hypobromite, and iodine nonionic surfactant complexes. Typically, bleach compositions range from about 0.5 to about 50, preferably from about 1 to about 10 weight percent bleaching agent and from about 50 to about 99.5, preferably from about 90 to about 99, weight percent aqueous liquid. The concentration of bleaching agent required will depend on the bleaching agent employed.

The term "aqueous liquid" refers to liquids which contain water. Included herein are substantially pure water, water containing inorganic salts, and aqueous alkaline and acidic solutions. Aqueous liquids include mixtures of water and water-miscible liquids, provided that the concentration of water-miscible liquids does not adversely affect the stability of the bleach composition or the viscelastic properties of the aqueous liquid. Also included herein are emulsions of immiscible liquids in water, and sprayable aqueous slurries of small sized solid particulates. Therefore, the aqueous liquids of this invention can contain fine particulate bentonites, silica, and/or calcium carbonate. Water, water containing inorganic salts and aqueous alkaline, and acidic solutions are preferred. Most preferred is an aqueous alkaline solution wherein the total electrolyte concentration is less than about 25, preferably less than about 10, weight percent of the aqueous liquid.

The aqueous liquid of this invention need not contain gritty materials, which are undesirable in some applications, to thicken the bleach composition. For example, gritty materials can be difficult to adequately remove from certain surfaces.

The term "mist" as it applies to aqueous liquids, means fine liquid droplets suspended in or falling through a moving or stationary gas atmosphere. Specifically, a mist provides an undesirable drift of aqueous droplets through a gas atmosphere. The properties of a mist are well known in the art and reference is made to Perry and Chilton, *Chemical Engineer's Handbook*, 5th Ed., Vol. 18, McGraw-Hill (1973), which is hereby incorporated by reference for a definition of mist and tests to determine properties of such exemplary mists. In distinguishing a mist from a spray, a mist is generally defined as a gas supsended liquid particle which has a diameter of less than about 10 $\mu$m, while a spray is a gas suspended liquid particle which has a diameter of greater than about 10 $\mu$m. However, it is understood that the specific size of spray and mist particles may vary depending upon the industrial use such as where a controlled droplet size is desired. As used herein, the terms "antimisting" and "non-misting" as applied to an aqueous liquid refers to the property which comprises the tendency of said liquid to not form a mist, i.e., undersized droplets that are easily gas suspended.

The terms "dispeners" and "dispensing device" refer to devices which can provide a stream or spray of the bleach composition as defined herein. Typically, the dispenser is a hand-held device. For example, the dispensing device can include a container for the bleach composition, a pump, and a spray-forming or stream-forming nozzle. The pump ejects the bleach composition from the container, through the nozzle, and into the atmopshere. Examples of suitable dispensing devices are disclosed in U.S. Pat. Nos. 4,463,905; 3,572,590; 3,985,271; 2,826,399; 4,013,228 and 4,153,208. The preferred dispensing devices have parts that are resistant to chemical attack by bleach. They also can include a suitable aerosol device that has a propellant, an atomizer, or both. Preferably, the aerosol device is one which forms a spray when employed.

Traditionally, engineers and scientists have been concerned with two separate and distinct classes of materials - the viscous fluid and the elastic solid. The simple linear engineering models, Newton's law for flow and Hooke's law for elasticity, worked well because most traditional materials (e.g., water, motor oil, and steel) fell in one of these two categories. However, as polymer science developed, scientists realized that these two categories represented only the extremes of a broad spectrum of material properties, and that polymers fell somewhere in the middle. As a result, polymer melts and solutions were characterized as "viscoelastic". The term "viscoelastic" refers to polymers that exhibit a combination of viscous (liquid-like) and elastic (solid-like) properties.

The phenomenon of viscoelasticity has been discovered in certain aqueous surfactant solutions. Surfactants consist of molecules containing both polar and nonpolar groups. They have a strong tendency to adsorb at surfaces or interfaces and thereby lower the surface or interfacial tension. Solutions of surfactants also form micelles, which are organized aggregates of the surfactants. A selected group of surfactant solutions also impart viscoelasticity to the solution as well. (See S. Gravsholt, *J. Coll. and Interface Sci.*, 57 (3) pp. 575-6 (1976), for a study of various surfactant compositions that impart viscoelasticity to aqueous solutions.) However, typical surfactant compositions will not inherently possess viscoelastic properties. As reported in H. Hoffman, *Advances in Coll. and Interface Sci.*, 17 pp. 276 (1982), surfactant compositions that impart viscoelastic properties to solutions are rare. Therefore, although all surfactant compositions will reduce surface tension, few will impart viscoelasticity. Those that do are known as "viscoelastic surfactants", and they possess desirable properties. It has been discovered that viscoelastic surfactants can be added to a water-based heat transfer fluid to improve its performance (U.S. Pat. No. 4,534,875).

Viscoelasticity is caused by a different type of micelle formation than the usual spherical micelles formed by most surfactant compositions. Viscoelastic surfactants form rod-like or cylindrical micelles. Although cylindrical micelles and spherical micelles have about the same diameter of 50 Å, cylindrical micelles can reach 1,000 to 2,000 Å in length and contain hundreds or thousands of individual surfactant molecules. This high degree of association requires a specific set of conditions that can only be achieved by matching the surfactant composition with a suitable solution environment. The solution environment will depend on factors such as the type and concentration of electrolyte and the structure and concentration of organic compounds present. Therefore, a surfactant composition may form cylindrical micelles in one solution to impart viscoelastic properties to it and form spherical micelles in another solution. The solution with spherical micelles will exhibit normal surfactant behavior and will not exhibit viscoelasticity. A determination of whether a solution is viscoelastic can be easily determined by empirical evaluation as described hereinafter.

The formation of long, cylindrical micelles in viscoelastic surfactants creates useful rheological properties. First, viscoelastic surfactants exhibit reversible shear thinning behavior. This means that under conditions of high stress, such as when the composition is sprayed through a nozzle, the composition will exhibit low viscosity. When the conditions of high stress are replaced with conditions of low stress, such as obtained when the composition has left the nozzle and is only subjected to gravitational force as it resides on a vertical surface, the composition will exhibit high viscosity. Secondly, viscoelastic surfactants will remain stable despite repeated high shear applications. Therefore, the thickened composition can be sprayed efficiently from a dispenser without undesirable mist and yet maintain its integrity on a vertical wall without running or dripping. Since typical polymeric thickeners will degrade when subjected to high shear, a bleach composition thickened with such a polymer will lose its integrity after repeated shearing.

The major test specified by the references discussed above to determine if an aqueous solution possesses viscoelastic properties consists of swirling the solution and visually observing whether the air bubbles created by the swirling recoil after the swirling is stopped. This has been the traditional test for many years. It is possible to quantify the degree of viscoelasticity a solution possesses by measuring the time required for the recoil motion to stop, as described in an article by J. Nash, *J. of Appl. Chem.*, 6, pp. 5440 (1956).

The surfactant compositions within the scope of this invention are ionic viscoelastic surfactants. The proper choice of counterion structure and solution environment give viscoelasticity. It has been discovered that certain viscoelastic surfactants will thicken a bleach composition without unduly sacrificing bleach stability. What follows is a discussion of ionic surfactant compounds and the counterions necessary to impart viscoelasticity to bleach compositions.

In general, ionic surfactant compounds comprise an ionic, hydrophilic moiety chemically bonded to a hydrophobic moiety (herein called a surfactant ion) and a counterion sufficient to satisfy the charge of the surfactant ion. Examples of such surfactant compounds are represented by the formula:

$$R_1(Y\oplus)X\ominus \text{ or } R_1(Z\ominus)A\oplus$$

wherein $R_1(Y\oplus)$ and $R_1(Z\ominus)$ represent surfactant ions having a hydrophobic moiety represented by $R_1$ and an ionic, solubilizing moiety represented by the cationic moiety $Y\oplus$ or the anionic moiety $Z\ominus$ chemically bonded thereto. $X\ominus$ and $A\oplus$ are the counterions associated with the respective surfactant ions.

In general, the hydrophobic moiety (i.e., $R_1$) of the surfactant ion is a hydrocarbyl or inertly substituted hydrocarbyl radical having one or more substituent groups, e.g., halo groups, which are inert to the aqueous liquid and components contained therein. Typically, the hydrocarbyl radical is an aralkyl group or a long chain alkyl or inertly substituted alkyl, which alkyl groups are generally linear and have at least about 12 carbon atoms. Representative long chain alkyl groups include dodecyl (lauryl), tetradecyl (myristyl), hexadecyl (cetyl), octadecyl (stearyl) and the derivatives of tallow, coco and soya. Preferred groups are generally alkyl groups having from about 14 to about 24 carbon atoms, with octadecyl, hexadecyl, and tetradecyl being the most preferred.

The cationic, solubilizing hydrophilic moieties or groups, i.e., $Y\oplus$, are generally onium ions wherein the term "onium ions" refers to a cationic group which is essentially completely ionized in water over a wide range of pH, e.g., pH values from about 2 to about 13. Representative onium ions include quaternary ammonium groups, i.e., $-N\oplus(R)_3$; tertiary sulfonium groups, i.e., $-S\oplus(R)_2$; quaternary phosphonium groups, i.e., $-P\oplus(R)_3$ and the like, wherein each R is individually a hydrocarbyl or inertly substituted hydrocarbyl. Of such cationic groups, the surfactant ion of the viscoelastic surfactants is preferably prepared having a quaternary ammonium group, i.e., $-N\oplus(R)_3$, with each R preferably being methyl or ethyl.

Representative anionic, solubilizing hydrophilic moieties or groups, herein designated $Z\ominus$, include sulfate groups, ether sulfate groups, sulfonate groups, carboxylate groups, phosphate groups, and phosphonate groups. Of such anionic groups, the surfactant ion of the viscoelastic surfactants is preferably prepared having a carboxylate or sulfate group. The most preferred anionic surfactant ion is an alkyl diphenyl ether disulphonate sold by The Dow Chemical Company, under the trademark "DOWFAX 2A1", especially where the alkyl group is octadecyl.

Fluoroaliphatic species suitably employed in the practice of this invention include organic compounds represented by the formula:

$$R_fZ^1$$

wherein $R_f$ is a saturated fluoroaliphatic moiety, preferably containing a $F_3C-$ moiety and $Z^1$ is an ionic moiety. The fluoroaliphatics can be perfluorocarbons. Suitable ionic moieties will be described hereinafter. The fluoroaliphatic moiety advantageously contains from about 3 to about 20 carbons wherein all can be fully fluorinated, preferably from about 3 to about 10 of such carbons. This fluoroaliphatic moiety can be linear, branched or cyclic, preferably linear, and can contain an occasional carbon-bonded hydrogen or halogn other than fluorine. More preferable are those linear perfluoroaliphatic moieties represented by the formula: $C_nF_{2n+1}$ wherein n is in the range of about 3 to about 10. An example of a linear perfluorocarbon that is stable to oxidation is $CF_3(CF_2)_pSO_3\ominus A\oplus$, wherein p is from about 2 to about 6. The method of its preparation is described in U.S. Pat. No. 2,732,398.

The counterions (i.e., $X\ominus$ or $A\oplus$) are organic ions that have a charge opposite that of the surfactant ions. The counterions and surfactant ions associate in the bleach composition and impart viscoelastic properties to it. Organic ions that are anionic serve as counterions for surfactant ions having a cationic, hydrophilic moiety; and the organic ions that are cationic serve as counterions for surfactant ions having an anionic, hydrophilic moiety. The organic counterions are formed by dissociation of the corresponding salts, acids, or bases.

The preferred anionic counterions are sulfonates or carboxylates. Representative of such anionic counterions which, when employed with a cationic surfactant ion, are capable of imparting viscoelastic properites to the bleach composition include various aromatic sulfonates such as p-toluene sulfonate and naphthalene sulfonate; and chlorobenzoic acid; and the like, where such counterions are water-soluble. Most preferred are p-toluene sulfonate; 3,4-dichlorobenzoate; and an alkyl diphenyl ether disulphonate sold by The Dow Chemical Company, under the trademakr "DOWFAX 2A1", especially where the alkyl group is octadecyl.

The cationic counterion may be an onium ion, most preferably a quaternary ammonium group. Representative cationic counterions in the form of a quaternary ammonium group include benzyl trimethyl ammonium or alkyl trimethyl ammonium wherein the alkyl group is advantageously octyl, decyl, dodecyl, cetyl, and the like. Most preferred is an alkyltrimethylammonium such as hexadecyltrimethylammonium supplied in the form of the bromide (HTAB). It is highly desirable to avoid stoichiometric amounts of surfactant ions and counterions when the alkyl groups of the counterions are large. The use of cationic counterions is generally less preferred than the use of anionic counterions.

The particular surfactants ions and counterions are selected so that the combination imparts viscoelastic properties to an aqueous liquid. Of the aforementioned surfactant ions and counterions, those combinations which form such viscoelastic surfactants will vary but are easily determined by the test methods hereinbefore described. Of the surfactant compounds which impart viscoelastic properties to an aqueous liquid, the preferred surfactant compounds include those represented by the formula:

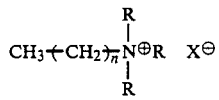

wherein n is an integer from about 13 to about 23, preferably an integer from about 15 to about 21; each R is independently an alkyl group, or alkylaryl, preferably independently methyl, ethyl or benzyl; and $X^\ominus$ is a p-toluene sulfonate. Especially preferred surfactant ions include cetyltrimethylammonium, myristyltrimethylammonium, and octadecyltrimethylammonium. Combinations of surfactant compounds can also be employed.

The viscoelastic surfactants are easily prepared by admixing the basic form of the desired cationic surfactants ions with a stoichiometric amount of the acidic form of the desired anionic counterions or by admixing the acidic form of the desired anionic surfactant ions with a soitchiometric amount of the basic form of the desired cationic counterions. Alternatively, stoichiometric amounts of the salts of the surfactant ions and counterions can be admixed to form the viscoelastic surfactant. See, for example, the procedures described in U.S. Pat. No. 2,541,816. Once the viscoelastic surfactant is prepared, the thickened bleach composition is prepared by admixing the viscoelastic surfactant with the bleach composition.

The concentration of viscoelastic surfactant required to impart viscoelastic properties to the bleach composition, where the viscoelasticity is measured by the techniques previously described, is that which measurably increases the viscosity of the composition. The type and concentration of viscoelastic surfactant required to increase the viscosity depends on the composition of the aqueous liquid, temperature, shear rate to which the bleach composition will be subjected, and the end use contemplated. In general, the requisite concentration of any specific viscoelastic surfactant is determined experimentally. Preferably, the concentration of viscoelastic surfactant ranges from about 0.05 to about 10 weight percent of the bleach composition. More preferably, the concentration of viscoelastic surfactant ranges from about 0.1 to about 2 weight percent of the bleach composition.

In a preferred embodiment of this invention, excess organic counterions are added to the bleach composition to further increase its viscosity, increase its viscosity stability at higher temperatures, or both. The counterions employed will have a charge opposite that of the surfactant ions and will dissolve in the bleach composition. Preferably, the excess organic counterions employed are the same as the counterions employed to associate with the surfactant ions to form the viscoelastic surfactant. However, the excess organic counterions can be different from the counterions which form the viscoelastic surfactant.

The concentration of excess organic counterions required to further increase the viscosity, increase the stability at higher temperatures, or both, will depend on the composition of the aqueous liquid, the surfactant ions and counterions employed, and the desired viscosity. Ordinarily, the concentration of excess counterions which will produce a noticeable effect range from about 0.1 to about 20, and more assuredly and preferably from about 0.5 to about 5, moles per mole of surfactant ions.

The bleach composition may contain an emulsion of an immiscible liquid, such as an oil or other organic ingredient, at a concentration ranging from about 0.05 to about 20 weight percent of the bleach composition. However, the concentration of immiscible liquid must be lower than that which will adversely affect the stability of the bleach composition. Viscoelastic surfactants employed in such emulsions tend to lose their viscoelasticity, possibly because the oil penetrates the micelles and destroys the aggregates required for viscoelasticity. Viscoelastic surfactants containing excess organic counterions maintain viscoelasticity in an emulsion longer than those without the excess organic counterions. Moreover, fluorinated viscoelastic surfactants maintain viscoelasticity in an emulsion longer at concentrations ranging up to about 50 weight percent, most preferably up to about 10 weight percent of the bleach composition.

The bleach compositions of this invention exhibit good bleach stability, phase stability, and viscosity stability. Good bleach stability refers to a thickened bleach composition that experiences less than 10 percent bleach degradation, which is the loss of the bleach active agent, for more than 30 days when stored under atmospheric conditions in a clear container in the dark at about 30° C. Good viscosity stability refers to a bleach composition that exhibits a viscosity at room temperature greater than 600 cps when subjected to a shear rate less than 5 sec$^{-1}$ more than 30 days after the composition is formulated and stored using the test conditions above. Good phase stability refers to the lack of development of separate phases for the bleach composition and viscoelastic surfactant until the bleach activity falls below useful values (for example, 75 percent bleach degradation).

If desired, the bleach composition can be a foam, which is a thickened liquid having a dispersion of gas therein. For example, the bleach composition can be vigorously agitated prior to use as a spray or stream. In addition, a surfactant, or other foam forming material can be used as an additive. Furthermore, a fine mesh screen device can be fitted over the nozzle of the dispensing device to intercept emitted bleach composition.

The following examples are presented to further illustrate but not limit the scope of this invention. All parts and percentages are by weight unless otherwise indicated.

EXAMPLE I

To 71.43 grams (g) of a commercially available NaOCl bleach formulation, sold by Gilbraltar National Corporation under the trademark "ROMAN BLEACH", which contains an aqueous liquid and 5.6 percent active NaOCl is added 27.45 g distilled water. To this solution is added 0.73 g hexadecyltrimethylammonium bromide and 0.39 g sodium p-toluene sulfonate. The mixture is agitated to the point at which a uniform viscoelastic solution results.

The sample is transferred to a polyethylene bottle which is sealed and placed in a constant temperature (31° C.) dark environment. Portions of the sample are periodically removed in order to evaluate the NaOCl concentration. The amount of NaOCl is determined using titration techniques employing sodium thiosulfate and starch/iodine indicator. Viscosity of the thickened bleach compositions are periodically evaluated using a Rheometrics Fluids Rheometer in a steady shear mode, and cone and plate configuration. Data are presented in Table I.

TABLE I

| | Percent of Original NaOCl Remaining after: | | | Viscosity of Composition (cp) after: | | | | | | | | |
|---|---|---|---|---|---|---|---|---|---|---|---|---|
| | | | | 4 hours Shear Rate (sec$^{-1}$) | | | 24 hours Shear Rate (sec$^{-1}$) | | | 35 days Shear Rate (sec$^{-1}$) | | |
| Sample | 19 days | 26 days | 40 days | 15.85 | 2.51 | 0.631 | 15.85 | 2.51 | 0.631 | 15.85 | 2.51 | 0.631 |
| Invention | 93.8 | 93.5 | 92.3 | 167 | 398 | 633 | 418 | 1076 | 2360 | 345 | 883 | 1879 |
| Comparison* | 96.5 | 95.8 | 94.3 | N.M. | N.M. | N.M. | N.M. | N.M. | N.M. | N.M. | N.M. | N.M. |

*Not an example of the invention. Sample is similar bleach formulation and distilled water but no viscoelastic surfactant. N.M. indicates that the viscosity of the composition is not measured, but the viscosity of the sample approximately equals that of an unthickened aqueous liquid (i.e., about 1 cp).

The data in Table I illustrate that the thickened formulation of this invention is shear thinning and exhibits excellent bleach stability over time as well as acceptable high viscosity stability. Conversely, a similar bleach composition thickened with 1 percent sodium polyacrylate rather than a viscoelastic surfactant experiences 84 percent reduction in viscosity after 18 days of similar treatment conditions. This is an unacceptably high rate of loss of thickening activity.

EXAMPLE 2

To 178.57 g of a commercially available NaOCl bleach formulation, sold by Gibraltar National Corporation under the Trademark "ROMAN BLEACH", which contains an aqueous liquid and 5.6 percent active NaOCl is added 166.45 g deionized water. To this solution is added 2.5 g hexadecyltrimethylammonium bromide and 2.5 g sodium p-toluene sulfonate.

The sample is transferred into a dispensing device which is generally described in U.S. Pat. No. 4,463,905. The screen in front of the nozzle is removed. A portion of the sample is sprayed onto a greasy vertical enamel painted surface and is observed to provide a good distribution of spray which uniformly covers the surface. The treated surface is cleaned by the sprayed bleach sample. The sample which is sprayed onto the vertical metallic surface is observed to adhere to said surface for several minutes (i.e., 10 minutes) without a substantial amount of dripping occurring. The screen in front of the nozzle is reattached to the dispensing device. A portion of the sample is sprayed onto the vertical glass surface as described hereinbefore. The sample which is sprayed onto the vertical glass surface forms a white, non-transparent, fairly thick foam; which foam adheres to the surface for several minutes (i.e., 10 minutes) without the occurence of substantial amounts of dripping. The sample is all three instances is applied as a spray wherein the dispensing device is operated without greater effort than is required for the spraying of essentially pure water. The bleach composition which is sprayed on the aforementioned surfaces is rinsed from the surface using water and no visible film remains on the surfaces.

EXAMPLE 3

A thickened bleach composition is prepared using the formulation and procedure of Example 1, except that sodium 3,4-dichlorobenzoate is substituted in an equimolar amount for sodium p-toluene sulfonate. The sample is transferred to a polyethylene bottle which is sealed and placed in a constant temperature (31° C.) dark environment. Samples of the composition are periodically evaluated using the techniques of Example 1. Data are presented in Table II.

TABLE II

| Percent of Original NaOCl Remaining After: | | | Viscosity of Composition (cp) when subjected to Shear Rate of 0.631 sec$^{-1}$ After: | | |
|---|---|---|---|---|---|
| 7 days | 35 days | 70 days | 24 hrs. | 7 days | 35 days |
| 100 | 87.8 | 62.3 | 3020 | 2780 | 1000 |

The data in Table II illustrate the carboxylate counterions can replace sulphonate counterions to form a viscoelastic surfactant. The bleach composition thickened with the viscoelastic surfactant exhibits excellent bleach stability and viscosity stability over time.

What is claimed is:

1. A method of thickening an aqueous bleach composition containing from about 1 to about 10 weight percent of a bleaching agent selected from the group consisting of hydrogen peroxide, potassium perchlorate, sodium hypochlorite, sodium peroxide, sodium chlorite, calcium hypochlorite, sodium hypobromite, and iodine nonionic surfactant complexes, comprising the step of contacting the composition with froma bout 0.05 to about 10 weight percent of a surfactant composition of onium surfactant ions and either aromatic sulfonate counterions or aromatic carboxylate counterions to form an aqueous solution under suitable solution conditions whereby the onium surfactant ions and aromatic counterions associate in the bleach composition to measurably increase the viscosity of the solution thereby forming a viscoelastic surfactant.

2. The method of claim 1 wherein the thickened composition produced is substantially nonmisting when sprayed.

3. The method of claim 1 further comprising the step of adding excess aromatic counterions at a concentration ranging from about 0.1 to about 20 moles per mole of surfactant ions.

4. The method of claim 1 wherein the thickened bleach composition produced exhibits good bleach stability, phase stability, and viscosity stability.

5. The method of claim 1 wherein the amount of viscoelastic surfactant formed ranges from about 0.1 to about 2 weight percent of the bleach composition.

6. The method of claim 1 wherein the onium surfactant ions comprise a hydrophilic moiety selected from the group consisting of quaternary ammonium groups and quaternary phosphonium groups.

7. The method of claim 6 wherien the hydrophilic moiety is a quaternary ammonium group.

8. The method of claim 7 wherein the counterions are aromatic sulfonate ions.

9. The method of claim 1 wherein the onium surfactant ions comprise a hydrophobic moiety containing a fluoroaliphatic group.

10. The method of claim 9 wherein the fluoroaliphatic group is linear.

11. The method of claim 10 wherein the fluoroaliphatic group is a perfluorocarbon group.

12. A thickened aqueous bleach composition made according to the method of claim 1 comprising from about 1 to about 10 weight percent of a bleaching agent selected from the group consisting of a hydrogen peroxide, potassium perchlorate, sodium hypochlorite, sodium peroxide, sodium chlorite, calcium hypochlorite, sodium hypobromite, and iodine nonionic surfactant complexes; from about 0.05 to about 10 weight percent of a surfactant composition of onium surfactant ions and either aromatic sulfonate counterions or aromatic carboxylate counterions, and water; the components of the composition being combined to form an aqueous solution under suitable solution conditions whereby the onium surfactant ions and aromatic counterions associate in the bleach composition to measurably increase the viscosity of the solution thereby forming a viscoelastic surfactant.

13. The composition of claim 12 wherein the thickened bleach composition is substantially nonmisting when sprayed.

14. The composition of claim 12 further comprising the addition of excess aromatic counterions at a concentration ranging from about 0.1 to about 20 moles per mole of surfactant ions.

15. The composition of claim 12 wherein the thickened bleach composition exhibits good bleach stability, phase stability, and viscosity stability.

16. The composition of claim 12 wherein the viscoelastic surfactant ranges from about 0.1 to about 2 weight percent of the bleach composition.

17. The composition of claim 12 wherien the onium surfactant ions comprise a hydrophilic moiety selected from the group consisting of quaternary ammonium groups and quaternary phosphonium groups.

18. The composition of claim 17 wherein the hydrophilic moiety is a quaternary ammonium group.

19. The composition of claim 18 wherein the counterions are aromatic sulfonate ions.

20. The composition of claim 12 wherein the onium surfactant ions comprise a hydrophobic moiety containing a fluoroaliphatic group.

21. The composition of claim 20 wherein the fluoroaliphatic group is linear.

22. The composition of claim 21 wherein the fluoroaliphatic group is a perfluorocarbon.

* * * * *